(12) United States Patent
Teramoto

(10) Patent No.: US 7,802,916 B2
(45) Date of Patent: Sep. 28, 2010

(54) DIFFERENTIAL SCANNING CALORIMETER

(75) Inventor: Yoshihiko Teramoto, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 348 days.

(21) Appl. No.: 11/961,944

(22) Filed: Dec. 20, 2007

(65) Prior Publication Data

US 2008/0151962 A1 Jun. 26, 2008

(30) Foreign Application Priority Data

Dec. 21, 2006 (JP) ............... 2006-343935

(51) Int. Cl.
*G01K 17/08* (2006.01)
*G01N 25/20* (2006.01)

(52) U.S. Cl. .............. 374/11; 374/29; 374/31; 374/141; 374/208; 374/1

(58) Field of Classification Search ............ 374/10–12, 374/29–39, 43–45, 135, 137, 4, 5, 141, 208, 374/163, 166, 1; 422/51; 436/147
See application file for complete search history.

(56) References Cited

U.S. PATENT DOCUMENTS

| | | | | |
|---|---|---|---|---|
| 4,530,608 A | * | 7/1985 | O'Neill | 374/11 |
| 5,099,441 A | * | 3/1992 | Mazzio | 702/136 |
| 5,288,147 A | * | 2/1994 | Schaefer et al. | 374/10 |
| 5,624,187 A | * | 4/1997 | Reading | 374/11 |
| 6,146,012 A | * | 11/2000 | Nakamura et al. | 374/10 |
| 6,422,742 B1 | * | 7/2002 | Kinoshita | 374/10 |
| 6,428,203 B1 | * | 8/2002 | Danley | 374/10 |
| 7,275,862 B2 | * | 10/2007 | Nishimura et al. | 374/11 |
| 7,677,795 B2 | * | 3/2010 | Schick | 374/10 |
| 2007/0189357 A1 | * | 8/2007 | Nishimura | 374/10 |
| 2008/0145840 A1 | * | 6/2008 | Eakin et al. | 435/6 |
| 2008/0187020 A1 | * | 8/2008 | Kinoshita | 374/10 |
| 2009/0034579 A1 | * | 2/2009 | Schick | 374/10 |
| 2010/0135853 A1 | * | 6/2010 | Broga et al. | 422/51 |

FOREIGN PATENT DOCUMENTS

| | | | |
|---|---|---|---|
| JP | 60207046 A | * | 10/1985 |
| JP | 05346413 A | * | 12/1993 |
| JP | 2000-28559 A | | 1/2000 |

* cited by examiner

*Primary Examiner*—Gail Verbitsky
(74) *Attorney, Agent, or Firm*—Brinks Hofer Gilson & Lione

(57) ABSTRACT

There is provided a differential scanning calorimeter for exactly measuring a calorie variation of the measured sample on the basis of the temperature difference between sample container and the reference container without the influence of the heat irregularity incoming from the surroundings and the noise components. The differential scanning calorimeter includes a heating furnace of an approximately H-shaped section having an approximately drum-shaped wall part and an approximately plate-shaped heat inflow part, a heater disposed outside the wall part so as to heat the heating furnace, a approximately bar-shaped heat-resistance member that is arranged along the center axis L of the wall part, that protrudes from both sides of the heat inflow part by an approximately equal length, that is made of a material heat conductivity lower than that of the material of the heating furnace, a sample container disposed at one end of the heat-resistance member, a reference container disposed at the other end of the heat-resistance member, and a differential heat flow detector measuring a difference between the temperature of the sample container and the temperature of the reference container as a measured value.

2 Claims, 3 Drawing Sheets

DIFFERENTIAL SCANNING CALORIMETER

RELATED APPLICATIONS

This application claims priority under 35 U.S.C. §119 to Japanese Patent Application No. JP2006-343935 filed Dec. 21, 2006, the entire content of which is hereby incorporated by reference.

BACKGROUND OF THE INVENTION

1. Field of the Invention

The present invention relates to a heat analysis apparatus for measuring the variation of the property of a sample according to the temperature variation. In Particular, the invention relates to a differential scanning calorimeter for measuring the amount of heat that a sample emits or absorbs in spare, compared with that of the reference sample on the basis of the temperature difference (differential heat) between the sample and a reference sample when the temperature of both of the samples varies.

2. Description of the Related Art

A differential scanning calorimeter is an apparatus for detecting differentially the amount of heat that a sample emits or absorbs in spare compared with a reference sample on condition that the measured sample and the reference sample to be stable thermally such as aluminum are arranged side by side when the temperature of both of the samples varies at constant rate. More specifically, the differential scanning calorimeter may include a cylinder-shaped heating furnace with a bottom plate, a heater for heating the heating furnace from the outer circumference, a heat buffer plate secured on the bottom plate of the heating furnace, a ring-shaper upper support plate and a lower support plate disposed on the heat buffer plate, a plate-shaped transmitting plate inserted between the upper support plate and the lower support plate to be secured by brazing and a sample container and a reference container placed on the heat transmitting plate (referring to JP-A-2000-28559). According to the above known apparatus, material with high heat conductivity such as silver is selected for the material of the heating furnace. In the meanwhile, in order to make the heat buffer plate and the heat transmitting plate, material with heat conductivity lower than that of the material for the heating furnace such as constantan is selected. According to the differential scanning calorimeter, heat of the heater is transmitted to the sample container and the reference container through the heat transmitting plate and the heat amount of the measured sample contained in the sample container can be detected differentially by measuring the temperature difference between both of the sample and reference containers. In particular, referring to JP-A-2000-28559, the heat of the heater can be transmitted to the heat transmitting plate via the heat buffer plate and the lower support plate from the heating furnace. Hence the temperature difference between the sample container and reference container can be avoided due to the occurrence of the temperature distribution over the heating furnace along the direction where the sample container and the reference container are arranged.

However, if the contact condition between the transmitting plates to install the sample container and the reference container and the ring-shaped lower support plate to transmit heat to the heat transmitting plate is not uniform in the known differential scanning calorimeter, as disclosed in JP-A-2000-28559, the heat amount of the sample container coming from the heat transmitting plate is not the same as that of the reference container. For example, if pores are formed in a potion of the blazing for securing the heat transmitting plate to the lower support plate, the heat conductivity of a portion with the pores may differ from that of a portion without pores.

That is, the amount of heat incoming from the sample container may differ from that incoming from the reference container due to the relationship of locations among the sample container, the reference container and the range of portion with pores. Therefore, the known apparatus has disadvantage that the amount of heat which the sample emits or absorbs in spare compared with that of the reference sample on the basis of the difference of both temperatures can not be detected exactly.

The heat emitted from the heater may contain noise components that perhaps differ place to place along the circumference of the heating furnace such as the fluctuation temperature. If the noise components are transmitted to the sample container and the reference container via the heating furnace, the heat buffer plate, the lower support plate and the heat transmitting plate from the heater, then the detected temperature difference may contain noise components due to the noise components of the incoming heat. Hence, the known apparatus has a problem that the amount of heat that the sample emits or absorbs in spare compared with that of the reference sample cannot be detected exactly.

SUMMARY OF THE INVENTION

An advantage of some aspects of the invention is to provide a differential scanning calorimeter that can detect exactly the calorie variation of the measured sample on the basis of the temperature difference between the sample container and the reference container without being influenced with the irregularity of heat incoming from the surrounding and the noise components.

In order to accomplish the above-mentioned advantage, the invention provides the following configurations.

According to an aspect of the invention, there is provided a differential scanning calorimeter including: a heating furnace of an approximately H-shaped cross section having an approximately drum-shaped wall part to cover the surroundings and an approximately plate-shaped heat inflow part to be formed at the inner circumference of the wall part; a heater disposed at the outer circumference of the wall part and to heat the heating furnace; an approximately bar-shaped heat-resistance member that is arranged along the center axis of the wall part of the heating furnace, that protrudes by an approximately equal length from both sides of the heat inflow part, that is secured at the heat inflow part, and that is made of a material with heat conductivity lower than that of the material of the heating furnace; a sample container disposed at one end of the heat-resistance member so as to contain a measured sample; a reference container disposed at the other end of the heat-resistance member; and a differential heat flow detector detecting a difference between the temperature of the sample container and the temperature of the reference container as a measured value.

According to this configuration, the heat emitted from the heater to the wall part of the heating furnace may be transmitted to the heat-resistance member secured to the heat inflow part via the heat inflow part from the wall part of the heating furnace. The heat transmitted to the heat-resistance member from the place secured at the heat inflow part is transmitted to both ends of the inner part of the heat-resistance member, and then transmitted to the sample container and the reference container. That is, each inflow route of heat transmitted to the sample container and the reference container is identical to each other from the each container to the place where the heat-resistance member is secured to the heat inflow part. Each inflow route to the sample container and the reference container beyond the place where the heat-resistance member is secured to the heat inflow part is different from each other, but the heat conditions such as sectional dimension and length of the heat inflow part is the same for each heat inflow route because the heat-resistance members made of the same material protrude by an approximately equal length from both sides of the heat inflow part of the heating furnace. Hence, heat is always supplied uniformly to the sample container and the reference container respectively regardless of the contact condition of the heating furnace and the heat-resistance member. Even though noise components are contained in the heat transmitted from the heater and the each temperature of the sample container and the reference container is fluctuated due to the influence of the noise components, each temperature fluctuation is offset when the difference of the temperature is measured by the differential heat flow detector.

According to another aspect of the invention, there is provided a differential scanning calorimeter including: a heating furnace of an approximately H-shaped cross section having an approximately drum-shaped wall part to cover the surroundings and an approximately plate-shaped heat inflow part to be formed at the inner circumference of the wall part; a heater disposed at the outer circumference of the wall part of the heating furnace so as to heat the heating furnace; a first heat-resistance member and a second heat-resistance member as a pair of bar-shaped members that is arranged along the center axis of the wall part of the heating furnace, that protrudes by an approximately equal length from the both sides of the heat inflow part, that is secured at the heat inflow part, and that is made of a material with heat conductivity lower than that of the material of the heating furnace; a sample container disposed at one end of the first heat-resistance member so as to contain a measured sample; a first reference container disposed at the other end of the first heat-resistance member; a second reference container disposed at one end of the second heat-resistance member protruding in the same direction as one end of the first heat-resistance member; a third reference container disposed at the other end of the second heat-resistance member; and a differential heat flow detector detecting a difference between a value obtained by subtracting the temperature of the first reference container from the temperature of the sample container and a value obtained by subtracting the temperature of the third reference container from the temperature of the second reference container as a measured value.

According to this configuration, heat is always supplied uniformly to the sample container and the first reference container, respectively, as described above. Even though the heat emitted from the heater is influenced with some noise components, the noise components are offset if evaluated as the value obtained by subtracting the temperature of the first reference container from the temperature of the sample container. Heat is always supplied uniformly to the second reference container and the third reference container, and some noise components are offset if evaluated as a value obtained by subtracting the temperature of the third reference container from the temperature of the second reference container. The differential heat flow detector may detect the difference between a value obtained by subtracting the temperature of the first reference sample container from the temperature of the sample container and the other value obtained by subtracting the temperature of the third sample container from the temperature of the second sample container. In this case, if the conditions of the reference samples in the first reference container and the third reference container are made identical, the difference between both containers indicates the temperature difference due to heat irregularly supplied from the different heat inflow routes in the sample container, the first reference container, the second reference container, and the third reference container. That is, the temperature difference between the measured sample contained in the sample container and the reference sample contained in the second reference container can be detected exactly by detecting the measured value in which the influence of the heat irregularity and the noise components are offset.

In the differential scanning calorimeter of the embodiment, it is preferable that the heating furnace is disposed with the center axis approximately vertical.

According to this configuration, the weight of each container and each sample contained in each container and the load to the heat-resistance member caused by the thermal expansion or thermal contraction corresponding to the temperature variation does not cause a warp but axis force because the heat-resistance member is arranged along the vertical direction. Hence, the sectional dimension of the heat-resistance member can be made minimum. The surface of each container to load the sample is approximately vertical to the direction where the heat-resistance member is arranged. Therefore, without considering the interference of the container and the heating furnace with the heat inflow part, the protruding length from both sides of the heat inflow part of the heat-resistance member can be suppressed to the minimum. The response time constant can be made short by raising the heat conductivity of the heat-resistance member, since the sectional dimension and the length of the heat-resistance member are in the minimum respectively.

According to the above-mentioned differential scanning calorimeter, the temperature difference between the sample container and the reference container can be detected exactly by installing the heat-resistance member without being influenced with the irregularity of heat coming from the surroundings and the noise components. As result, the calorie variation of the measured sample can be measured exactly on the basis of the temperature difference between the sample container and the reference container.

DESCRIPTION OF THE PREFERRED EMBODIMENTS

Figure 1:
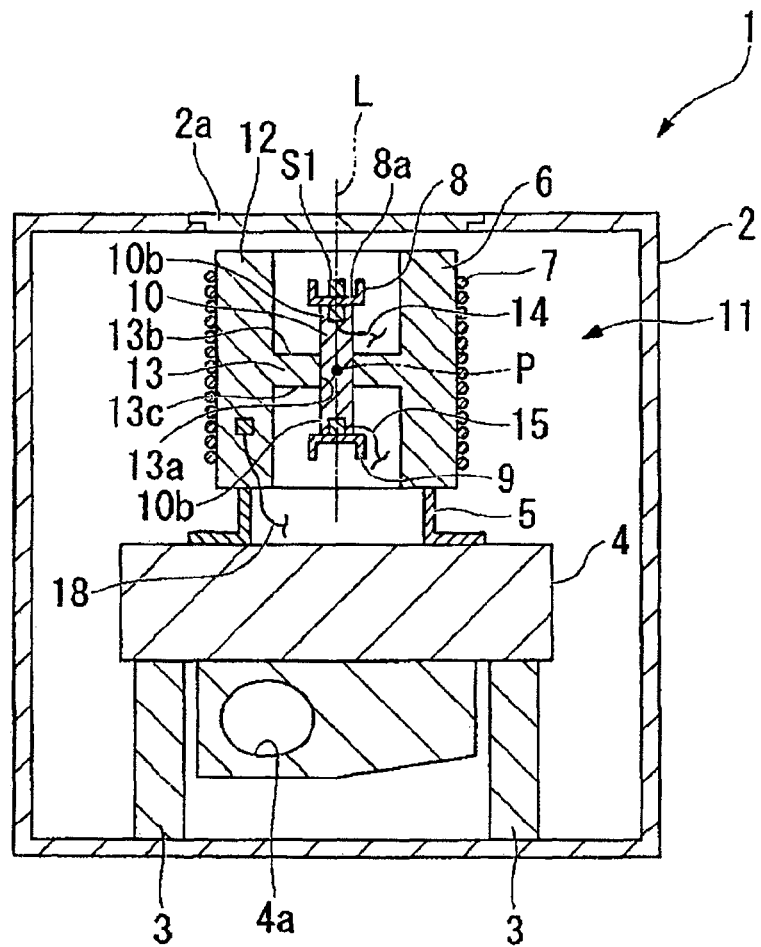
FIG. 1 shows a perspective view of a differential scanning calorimeter according to a first embodiment of the invention.
Figure 2:
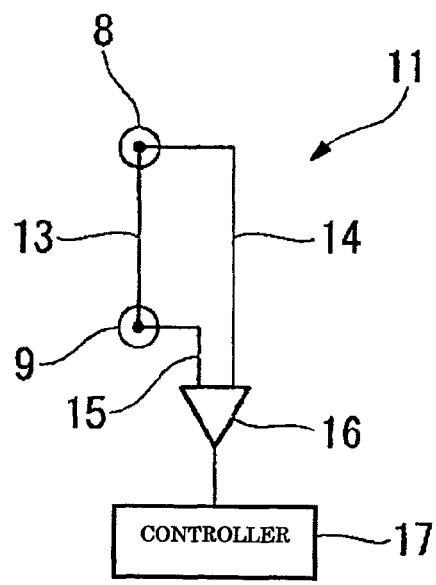
FIG. 2 shows a wiring diagram of the differential heat flow detector according to the first embodiment of the invention.

FIGS. 1 and 2 show an embodiment of the invention. Referring to the FIG. 1, the differential scanning calorimeter 1 of the embodiment according to the invention includes a furnace case 2, a cooling block 4 supported by a leg 3 within the furnace case 2, a heat sink (heating furnace) 6 supported by a heat-resistance element 5 on the cooling block 4 and a heater 7 heating the heat sink 6. The heat sink 6 includes a sample container 8, a reference container 9, a heat-resistance member 10 supporting the sample container 8 and the reference container 9 and a differential heat flow detector 11 detecting the temperature difference of the sample container 8 and the reference container 9. Each component will be described in detail in the following.

The furnace case 2 has a cover 2a to exchange samples in and out and to shield the inner volume from the out for avoiding the occurrence of the heat convection within the inner of the furnace case 2 where the specimen is disposed. The cooling block 4 cools the heat sink 6 using the heat-resistance element 5 as a heat inflow route. Hence the cooling block 4 may be made of preferably a high conductivity material to inflow uniformly heat to the heat-resistance element 5, and for example the cooling block 4 may be made of pure aluminum. An insertion hole 4a is disposed in the cooling block 4 and the entire cooling block 4 is cooled by inserting a cooling head of an electrical refrigerator not shown in the figure into the insertion hole 4a, thereby cooling the heat sink 6. For cooling the cooling block 4, the cooling method may not be limited to an electric cooling such as the above-mentioned electric refrigerator, but a gas cooling method in which an extreme low temperature gas is blown within the cooling block 4 may be employed. The heat-resistance element 5 which is approximately in shape of a cylinder with a flange supports the heat sink 6 apart by a predetermined distance from the cooling block 4. The dimension and material of the heat resistant element 5 may be determined by considering the heating efficiency of the heater 7 and the cooling efficiency of the cooling block 4. For example, stainless alloy metal may be used as the material.

The heat sink 6 which is approximately in shape of a cylinder has a wall part 12 to cover the surroundings of the sample container 8 and the reference container 9 and a heat inflow part 13 which has an approximately plate shape and which is disposed inside the wall part 12, whereby the sectional view of the heat sink 6 is made in an H shape. The heat sink 6 is supported by the heat-resistance element 5 with the center axis L of the wall 12 approximately vertical. The heater 7 connected to a power supply (not shown in Figs) serves as a power transmitting line, and can heat all the wall part 12 by being turn-winded around the wall part 12 of the heat sink 6. The heat sink 6 may be made of a material with high heat conductivity such as pure silver, which makes it possible to supply uniformly heat emitted from all the heater 7 to the sample container 8 and the reference container 9 and in turn to supply uniformly heat emitted from the sample container 4 and the reference container 5 to the cooling block 4.

The heat-resistance member 10 which is approximately in shape of a bar with uniform sectional dimension is secured to the heat inflow part 13 through the through-hole 13a of the heat inflow part 13 of the heat sink 6. More specifically, the heat-resistance member 10 is arranged along the center axis L of the heat sink 6 in vertical direction. The heat-resistance member 10 protruding by an equal length from both sides 13b, 13c of the heat inflow part 13 of the heat sink 6 is secured to the heat inflow part 13 of the heat sink 6 by, for example, silver-alloy brazing. A material for the heat-resistance member 10 has heat conductivity lower than that for the heat sink 6, for example constantan may be selected for the heat-resistance member 10. The sample container 8 containing a measured sample S1 is secured to the upper end 10a of the heat-resistance member 10 to make the load surface 8a for loading the measured sample S1 approximately horizontal. The reference container 9 corresponding to the reference sample may be made of the same material and shape as the sample container 8 and secured to the lower end 10b of the heat-resistance member 10.

A thermoelectric-couple fine line 14 formed of chromel is welded to the sample container 8, and a thermoelectric-couple intersection point is formed. A thermoelectric-couple fine line 15 formed of chromel is welded to the reference container 9 and a thermoelectric-couple intersection point is formed. As shown in FIG. 2, the thermoelectric-couple fine lines 14 and 15 are connected to an amplifier 16, which forms the thermoelectric-couple between the sample container 8 and the reference container 9. A controller 17 is connected to the output of the amplifier 16. Hence the controller 17 are input differentially from the heat transmitting hand 14 and 15, a measured value ΔT corresponding to the difference between the temperature Ts of the sample container 8 and the temperature T1 of the reference container 9 may be detected with the amplified output by the amplifier 16, as shown in Equation 1, that is, the thermoelectric-couple fine line 14 and 15, the amplifier 16 and the controller 17 constitute a differential heat flow detector 11. The controller 17 may measure a calorie variation of the measured sample S1 contained in the sample container 8 on the basis of the detected value, namely, the temperature difference between the sample container 8 and the reference container 9. A controlled thermoelectric-couple 18 is disposed at the heat sink 6 to measure the temperature of the heat sink 6 and to be connected to the controller 17. The temperature of the heat sink 6 can be set to a given value by heating and cooling it with the heater 7 and the cooling block 4 under the control of the controller 17.

$$\Delta T = Ts - T1 \qquad \text{Equation 1}$$

In turn, the operation of the differential scanning calorimeter will be described by demonstrating the measurement of the calorie variation of the measured sample S1. In this explanation, it is assumed that the reference sample is not arranged in the reference container 9 resulting to arrangement of the reference container 9 alone. At first, the cover 2a of the furnace case 2 is removed to contain a necessary sample S1 into the sample container 8 and then the cover 2a is recovered for closing the sample container 8. The measurement is initiated. The controller 17 supplies power to the heater 7 on the basis of a preset temperature program and the temperature of the heat sink 6 detected from the output of the controlled thermoelectric-couple 18, and raises the temperature of the heat sink 6. The heat emitted from the heater 7 is transmitted to all the wall part 12 of the heat sink 6. The heat transmitted to the wall part 12 is transmitted to the heat-resistance member 10 from a location P which is fixed to the heat inflow part in the heat-resistance member 10, that is, the through-holes 13a via the heat inflow part 13. The heat transmitted to the heat-resistance member 10 via the through-hole 13a is transmitted to the upper end 10a and lower end 10b within the heat-resistance member 10, and transmitted to the sample container 8 and the reference container 9. The heat transmitted to the sample container 8 raises the temperature of the sample container 8 and the temperature of the measured sample S1. The heat transmitted to the reference container 9 raises the temperature of the reference container 9. The differential heat flow detector 11 detects the temperature difference between the sample container 8 and the reference container 9 as measures to detect the temperature difference caused by the property difference between the measured sample S1 and the reference sample (non-existence), on the basis of which the calorie of the measured sample S1 is measured differentially.

In the above-mentioned example, each inflow route of the heat transmitted to the sample container 8 and the reference container 9 is the same, that is, a single passage which leads to the location P fixed at the through-hole 13a of the heat inflow part 13 in the heat-resistance member 10 from the heater 7 via the wall part 12 of the heat sink 6 and the heat inflow part 13 is utilized for transmitting heat to the sample container 8 and the reference container 9. In the heat-resistance member 10, each passage which leads to the upper end 10a and the lower end 10b where the sample container 8 and the reference container 9 is secured respectively is constructed with an identical material, equal cross section and equal inflow route with the same length, which makes each passage equal heat condition. Even though the contact condition of the circumference direction of the heat-resistance member 10 is different from each other, for example a partially bad contact between the heat inflow part 13 of the heat sink 6 and the heat-resistance member 10 or formation of pores in a part of the brazing, an equal amount of heat is transmitted to the sample container 8 and the reference container 9, respectively.

If the heat transmitted from the heater 7 contains noise components such as temperature fluctuation, each temperature of the sample container 8 and the reference container 9 varies with the influence of the noise components. However, according to the embodiment of the present invention, each inflow route for the heat transmitted to the sample container 8 and the reference container 9 is in the equal condition in which each route from the heater 7 to the location P to which the heat-resistance member 10 is secured and the routes to the upper end 10a and the lower end 10b are identical in thermal condition. Accordingly, each temperature variation of the sample container 8 and the reference container 9 is synchronized, by which each temperature fluctuation due to the noise components is offset when the differential heat flow detector 11 detects the difference of the both temperatures as measures.

As described above, in the differential scanning calorimeter 1 according to the embodiment of the invention, an equal amount of heat is always supplied to the sample container 8 and the reference container 9, and also the noise components due to the heater 7 is removed when the differential heat flow detector 11 detects. Hence the temperature difference between the sample container 8 and the reference container 9 is detected exactly without being influenced with the irregularity of heat incoming from the surroundings and the noise components. As result, the calorie variation of the measured sample S1 is measured exactly on the basis of the temperature difference of the sample container 8 and the reference container 9.

In the meanwhile, the heat sink 6 and the heat-resistance member 10 are made of different materials and have different thermal expansion coefficients. The thermal expansion and the thermal contraction are repeated due to a wide variation in temperature of the heater 7 and the cooling block 4 at the time of measurement. Hence, some stress accompanied with the temperature variation occurs at the fixed portion of the heat sink 6 and the heat-resistance member 10. However, in the differential scanning calorimeter 1 according to the embodiment of the invention, the fixation of the heat sink 6 and the heat-resistance member 10 such as brazing is made by only a partial fixation at the through-hole 13a of the heat inflow part 13. Hence, the occurrence of the stress accompanied with the temperature variation at the fixation may be suppressed and the durability of the apparatus may be improved by the prevention of the heat degradation.

In the differential scanning calorimeter 1 according to the embodiment of the invention, the heat-resistance member 10 is arranged along the center axis L of the wall part 12 of the heat sink 6 and the sample container 8 and the reference container 9 are arranged along the center axis L. Hence, the outer diameter of the heat sink 6 is smaller than that of the known art. As result, the temperature distribution of the heat sink 6 in itself is narrow and the heat capacity of the heat sink 6 is small and hence the improvement of the heating rate and cooling rate is possible.

Furthermore, because the heat-resistance member 10 is arranged approximately vertically along the center axis L of the wall part 12 of the heat sink 6, the load acting to the heat-resistance member 10 due to the weight of the sample container 8 and the reference container 9, the weight of the sample contained in each container, and the thermal expansion or thermal contraction corresponding to the temperature variation does not cause a warp but serves as an axis force. Hence, the cross section of the heat-resistance member 10 is made to be the minimum. Since the surface for loading the sample of each container is approximately horizontal, the heat-resistance member 10 is vertical to the arrangement direction. Hence, not considering the interference among the sample container 8, the reference container 9 and the heat inflow part 13 of the heat sink 6, the length of the part protruding from both sides 13b, 13c of the heat inflow part 13 of the heat-resistance member 10 can be made to be the minimum. Since the cross section and the length of the heat-resistance member 10 can be made to be in the minimum, the response time constant can be made to be short by increase of the heat conductivity of the heat-resistance member 10.

In the above mentioned embodiment of the invention, such case that the temperature of the differential scanning calorimeter is raised by heater 7 is illustrated as an example, however, the invention is not limited to the case, but intends to include a case that the differential scanning calorimeter is cooled by the cooling block 4, resulting to the drop of the temperature.

Second Embodiment

Figure 3:
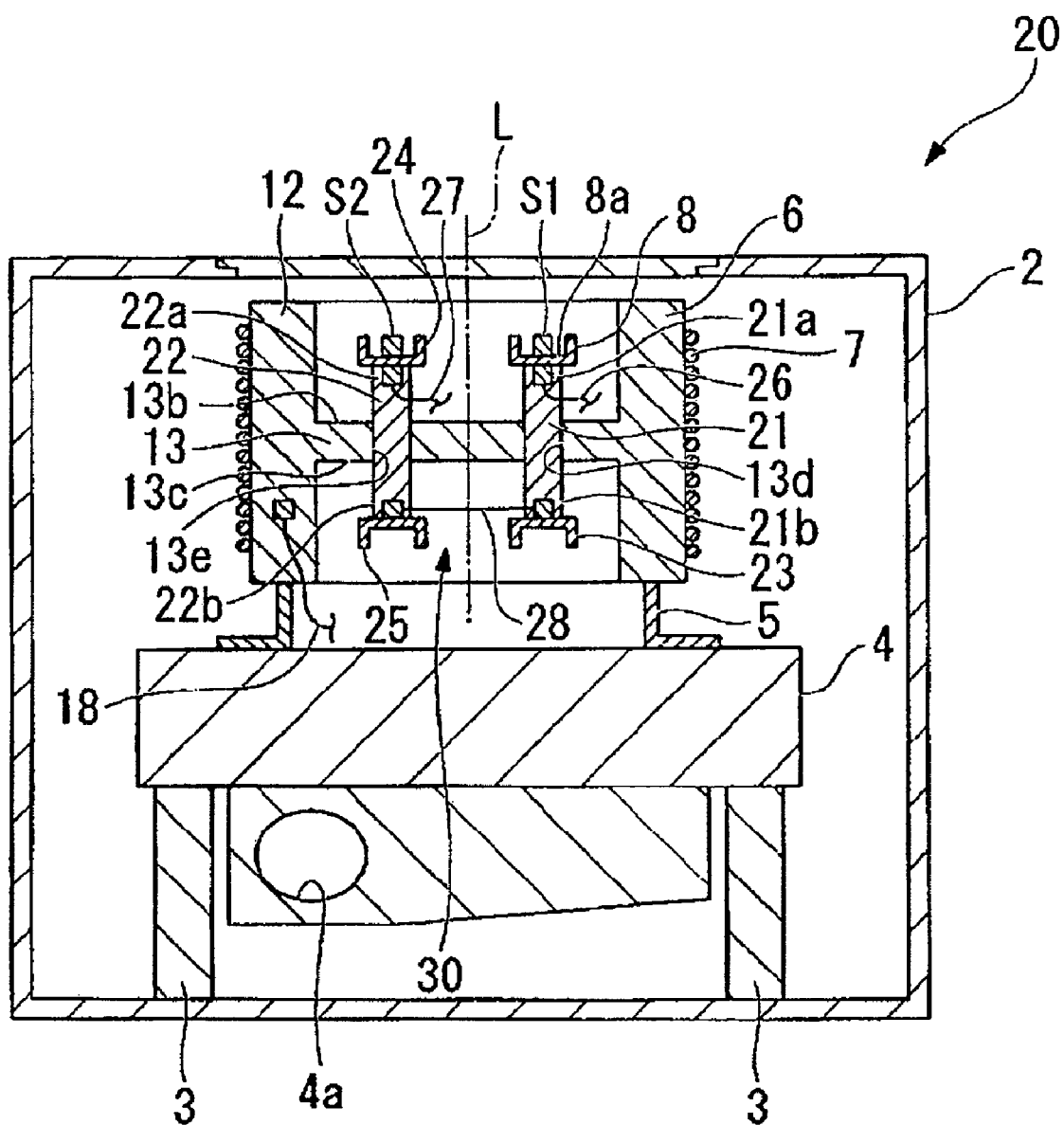
FIG. 3 shows a perspective view of the differential scanning calorimeter according to a second embodiment of the invention.
Figure 4:
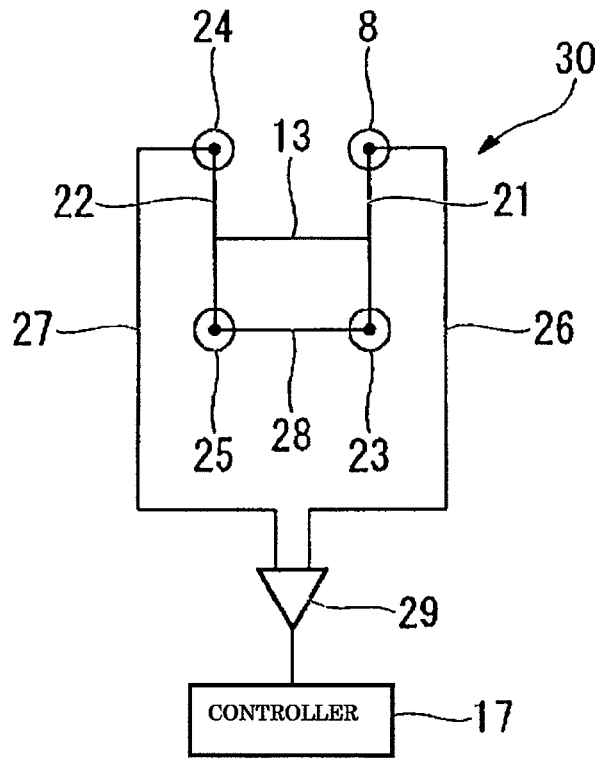
FIG. 4 shows a wiring diagram of the differential heat flow detector according to the second embodiment of the invention.

FIGS. 3 and 4 show a second embodiment of the invention. In the second embodiment of the invention, the same elements as those of the first embodiment are denoted by the same numerals and explanation thereof will be omitted.

In a differential scanning calorimeter 20 according to the second embodiment of the invention, a pair of through-holes 13d and 13e are formed at the heat inflow part 13 of the heat sink 6, and the first heat-resistance member 21 and the second heat-resistance member 22 are secured at the heat inflow part 13 penetrating the corresponding through-holes 13d and 13e, respectively. The first heat-resistance member 21 and the second heat-resistance member 22 have an approximately bar shape with a uniform section, and may be made of a material which has heat conductivity lower than that of the material of the heat sink 6. For example, the heat-resistance members 21 and 22 may be made of constantan. The first heat-resistance member 21 and the second heat-resistance member 22 are approximately vertical along the center axis L of the wall part 12 of the heat sink 6. The heat-resistance members 21 and 22 protrude by an approximately equal length from both sides 13b and 13c of the heat inflow part 13 so as to be secured at the heat inflow part 13.

The sample container 8 is secured to the upper end 21a of the first heat-resistance member 21 and the first reference container 23 is secured to the lower end 21b thereof. The second reference container 24 is secured to the upper end 22a of the second heat-resistance member 22 and a third reference container 25 is secured to the lower end 22b thereof. In this case, the first reference container 23, the second reference container 24 and the third reference container 25 are made of the same material and shape as the sample container 8.

A thermoelectric-couple fine line 26 formed of chromel is welded to the sample container 8 and the thermoelectric-couple intersection point is formed. A thermoelectric-couple fine line 27 formed of chromel is welded to the second reference container 24 and the thermoelectric-couple intersection point is formed. Both ends of a thermoelectric-couple fine line 28 formed of chromel respectively is welded to the first reference container 23 and the third reference container 25 to form an intersection point. As shown in FIG. 4, among those thermoelectric-couple fine lines, the thermoelectric-couple fine lines 26 and 27 corresponding to the sample container 8 and the second reference container 24 are connected to a amplifier 29, by which a thermoelectric-couple is constructed among the sample container 8, the first reference container 23, the third reference container 25, and the second reference container 24. The output of the amplifier 29 is connected to a controller 17. The controller 17 may detect the difference ΔT between a value obtained by subtracting the temperature T1 of the first reference container 23 from the temperature Ts of the sample container 8 and another value obtained by subtracting the temperature T3 of the third reference container 25 from the temperature T2 of the second reference container 24 as a measured value with the output amplified by the amplifier 29 after being input differentially from the thermoelectric-couple fine line 26 and 27, as shown in Equation 2, that is, a differential heat flow detector 30 may be constituted from the thermoelectric-couple fine line 26, 27, and 28, the amplifier 29 and the controller 17.

$$\Delta T = (Ts-T1)-(T2-T3) \quad \text{Equation 2}$$

In turn, the operation of the differential scanning calorimeter 20 will be described by demonstrating the measurement of the calorie variation of the measured sample S1. Regarding the reference sample, the reference sample S2 is contained in the second reference container 24, unlike the measured sample S1, and the condition of the reference sample is made to be equal by not arranging the reference sample in the first reference container 23 and the third reference container 25.

That is, as described in the first embodiment, the controller 17 supplies a given power to the heater 7 on the basis of the preset temperature program and the temperature of the heat sink 6 detected from the output of the controlled thermoelectric-couple 18 to elevate the temperature of the heat sink 6. The differential heat flow detector 30 detects the difference between a value obtained by subtracting the temperature of the first reference container 23 from the temperature of the sample container 8 with the measured sample S1 and another other value obtained by subtracting the temperature of the third reference container 25 from the temperature of the second reference container 24 with the reference sample S2 as a measured value.

In this case, similar to the first embodiment, heat is always uniformly supplied between the sample container 8 and the first reference container 23. Even under the influence of the noise component of the heat emitted from the heater 7, the noise component is cancelled with the value obtained by subtracting the temperature of the first reference container 23 from the temperature of the sample container 8. Similarly, heat is always uniformly supplied between the second reference container 24 and the third reference container 25. The noise component is cancelled with the value obtained by subtracting the temperature of the third reference container 25 from the temperature of the second reference container 24. The first reference container 23 and the third reference container 25 have the same reference sample condition. Hence, the difference between both temperatures results not from the different samples, but from the difference in temperature due to the irregularity of the supplied heat which is caused by the difference of the heat inflow route between the sample container 8 and the first reference sample 23 disposed at the first heat-resistance member 21 and the second reference container 24 and the third reference container 25 disposed at the second heat-resistance member 22. That is, the temperature difference between the measured reference sample S1 contained in the sample container 8 and the reference sample S2 contained in the second reference container 23 can be detected exactly subtracting the influence of the heat irregularity and the noise components by means of the detection of the measure. Hence, the calorie variation of the measured sample S1 can be measured exactly on the basis of the temperature difference.

Figure 5:
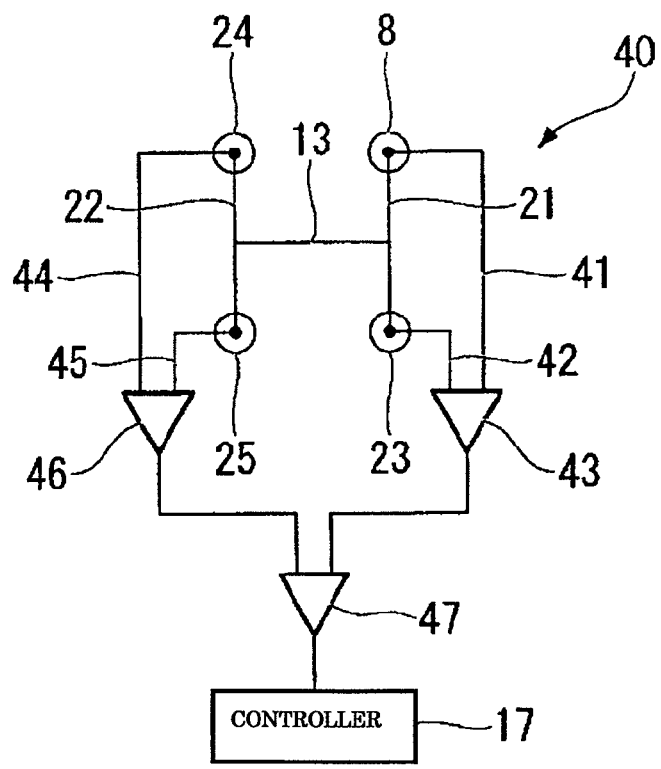
FIG. 5 shows a wiring diagram of the differential heat flow detector according to a modified example of the second embodiment of the invention.

FIG. 5 shows a modified example of the wiring of the thermoelectric-couple fine line constituting the differential heat flow detector in the differential scanning calorimeter according to the embodiment of the invention. In the differential heat flow detector 40 of the modified embodiment, the thermoelectric-couple fine lines 41 and 42 formed of chromel are welded to the sample container 8 and the first reference container 23, respectively, to form the thermoelectric-couple intersection point. The thermoelectric-couple fine lines 41 and 42 are connected to the first amplifier 43. Similarly, the thermoelectric-couple fine lines 44 and 45 formed of chromel are welded to the second reference container 24 and the third reference container 25, respectively, and are connected to a second amplifier 46. The outputs of the first amplifier 43 and the second amplifier 46 are connected to a third amplifier 47, whereby the controller 17 can detect the output of the third amplifier 47.

In this case, a thermoelectric-couple is formed between the sample container 8 and the first reference container 23, and the first amplifier 43 outputs the temperature difference between the sample container 8 and the first reference container 23. Similarly a thermoelectric-couple is formed between the second reference container 24 and the third reference container 25, and the second amplifier 46 outputs the temperature difference between the second reference container 24 and the third reference container 25. The third amplifier 47 outputs the output difference between the first amplifier 43 and the second amplifier 46, that is, the difference between a value obtained by subtracting the temperature of the first reference container 23 from the temperature of the sample container 8 and another value obtained by subtracting the temperature of the third reference container 25 from the temperature of the second reference container 24, as described above. The controller 17 can detect the difference as the measured value. According to the modified embodiment of the first amplifier 43 and the second amplifier 46 corresponding to one interval between the sample container 8 and the first reference 23 and the other interval between the second reference container 24 and the third reference container 25 are disposed respectively. The differential input value which is input to the third amplifier 47 is regulated by adjusting the amplified rate of the first amplifier 43 and the second amplifier 46. Hence, even though a fine difference of a heat electromotive force may occur due to one thermoelectric-couple formed between the sample container 8 and the first reference container 23 and the other thermoelectric-couple formed between the second reference container 24 and the third reference container 25, the temperature difference between the sample container 8 and the second reference container 24 is detected exactly by adjusting each amplified rate of the first amplifier 43 and the second amplifier 46.

In the foregoing, the embodiments of the invention are described in detail referring to the accompanied drawings, however, the substantial constitution is not limited to the embodiments and includes the modified invention within the scope of the invention.

What is claimed is:

1. A differential scanning calorimeter comprising:
a heating furnace of an approximately H-shaped cross section having an approximately drum-shaped wall part to cover the surroundings and an approximately plate-shaped heat inflow part to be formed at the inner circumference of the wall part,
wherein the heating furnace is disposed with a center axis approximately vertical;
a heater disposed at the outer circumference of the wall part and to heat the heating furnace;
an approximately bar-shaped heat-resistance member that is vertically arranged along the center axis of the heating furnace, that protrudes by an approximately equal length from both sides of the heat inflow part, that is secured at the heat inflow part, and that is made of a material with heat conductivity lower than that of the material of the heating furnace;
a sample container disposed at one end of the heat-resistance member so as to contain a measured sample;
a reference container disposed at an opposite end of the heat-resistance member; and a differential heat flow detector detecting a difference between the temperature of the sample container and the temperature of the reference container as a measured value.

2. A differential scanning calorimeter comprising,
a heating furnace of an approximately H-shaped cross section having an approximately drum-shaped wall part to cover the surroundings and an approximately plate-shaped heat inflow part to be formed at the inner circumference of the wall part;
a heater disposed at the outer circumference of the wall part of the heating furnace and to heat the heating furnace,
wherein the heating furnace is disposed with a center axis approximately vertical;
a first heat-resistance member and a second heat-resistance member as a pair of bar-shaped members that are vertically arranged along the center axis of the heating furnace, that protrude by an approximately equal length from the both sides of the heat inflow part, that are secured at the heat inflow part, and that are made of a material with heat conductivity lower than that of the material of the heating furnace;
a sample container disposed at one end of the first heat-resistance member so as to contain a measured sample;
a first reference container disposed at an opposite end of the first heat-resistance member;
a second reference container disposed at one end of the second heat-resistance member protruding in the same direction as one end of the first heat-resistance member;
a third reference container disposed at an opposite end of the second heat-resistance member; and
a differential heat flow detector detecting a difference between a value obtained by subtracting the temperature of the first reference container from the temperature of the sample container and a value obtained by subtracting the temperature of the third reference container from the temperature of the second reference container as a measured value.

* * * * *